United States Patent
Bieberschulte et al.

(10) Patent No.: US 10,179,138 B2
(45) Date of Patent: Jan. 15, 2019

(54) PHARMACEUTICAL COMPOSITION COMPRISING 7β-HYDROXYCHOLESTEROL INTRAVENOUS ADMINISTRATION

(71) Applicant: Immunopharm AG, Balzers (LI)

(72) Inventors: Werner Bieberschulte, Eschen (LI); Christine Grimm, Gailingen (DE); Rohan Charles Fernando, Heidelberg (DE)

(73) Assignee: IMMUNOPHARM AG, Balzers (LI)

( * ) Notice: Subject to any disclaimer, the term of this patent is extended or adjusted under 35 U.S.C. 154(b) by 0 days.

(21) Appl. No.: 15/404,591

(22) Filed: Jan. 12, 2017

(65) Prior Publication Data
US 2017/0196894 A1 Jul. 13, 2017

(30) Foreign Application Priority Data

Jan. 12, 2016 (EP) .................................. 16000071

(51) Int. Cl.
*A61K 31/575* (2006.01)
*A61K 9/00* (2006.01)
*A61K 9/08* (2006.01)
*A61K 47/02* (2006.01)
*A61K 47/10* (2017.01)
*A61K 47/20* (2006.01)
*A61K 47/26* (2006.01)
*A61K 47/44* (2017.01)

(52) U.S. Cl.
CPC .......... *A61K 31/575* (2013.01); *A61K 9/0019* (2013.01); *A61K 9/08* (2013.01); *A61K 47/02* (2013.01); *A61K 47/10* (2013.01); *A61K 47/20* (2013.01); *A61K 47/26* (2013.01); *A61K 47/44* (2013.01)

(58) Field of Classification Search
CPC .................................................... A61K 31/575
See application file for complete search history.

(56) References Cited

U.S. PATENT DOCUMENTS

| | | | | |
|---|---|---|---|---|
| 4,442,037 A | * | 4/1984 | Arakawa | C07J 41/0055 530/363 |
| 6,011,062 A | * | 1/2000 | Schneider | A61K 31/5575 514/530 |
| 2015/0361125 A1 | * | 12/2015 | Covey | C07J 21/00 514/178 |
| 2017/0196892 A1 | * | 7/2017 | Benner | A61K 31/575 |

FOREIGN PATENT DOCUMENTS

EP 2522350 A1 11/2012

OTHER PUBLICATIONS

De Caprio, J. et al., "Bile acid and sterol solubilization in 2-hydroxypropyl-beta-cyclodextrin", Journal of Lipid Research vol. 33, 1992, pp. 441-443.
Larsson, H. et al., "In Vivo Interconversion of 7beta-Hydroxycholesterol and 7-Ketocholesterol, Potential Surrogate Markers for Oxidative Stress", Free Radical Biology & Medicine 43 (2007), May 10, 2007, pp. 695-701.

* cited by examiner

*Primary Examiner* — Zohreh A Fay
(74) *Attorney, Agent, or Firm* — Perkins Coie LLP; Viola T. Kung

(57) ABSTRACT

The present invention relates to a pharmaceutical composition comprising (a) 7β-hydroxycholesterol, (b) a water soluble organic solvent, preferably propylene glycol and/or DMSO, and (c) a solubilizing agent, preferably PEG hydrated castor oil, and to a method for preparing the same. This composition is suitable for preparing an intravenously administered preparation and comprises the pharmaceutically active substance β-hydroxycholesterol, which is poorly soluble in water.

8 Claims, No Drawings

123
PHARMACEUTICAL COMPOSITION COMPRISING 7β-HYDROXYCHOLESTEROL INTRAVENOUS ADMINISTRATION

This application claims priority of European Application No. 16000071.7, which was filed on Jan. 12, 2016.

FIELD OF THE INVENTION

The present invention relates to a pharmaceutical composition comprising (a) 7β-hydroxycholesterol, (b) at least one water soluble organic solvent, and (c) a solubilizing agent; and to a method for preparing the same. This composition is suitable for preparing an intravenously administered preparation and comprises the pharmaceutically active substance β-hydroxycholesterol, which is poorly soluble in water.

BACKGROUND OF THE INVENTION

The preparation of pharmaceutical compositions requires a suitable solvent or carrier system for dispersing the pharmaceutically active substance so that the composition can be administered to a patient. The solvent must be able to solve or dissolve a therapeutically effective amount of the active substance to provide an active composition. However, many pharmaceutically active compositions are not sufficiently soluble in solvents, such as in water. Another problem is that many pharmaceutical active substances become unstable when diluting them for an infusion solution or they exhibit decomposition or loss of activity of the active substance during storage in a solvent system. The poor solubility and the susceptibility to decomposition highly limit the use of these pharmaceutically active substances, which are poorly soluble in water, in therapy.

Most of the currently available dosage forms of the pharmaceutically active substance 7β-hydroxycholesterol are capsules for oral administration because 7β-hydroxycholesterol is insoluble in water.

However, there is an approach for the preparation of 7β-hydroxycholesterol in a water soluble form. The application DE 35 07 721 A1 describes a method for the preparation of water soluble derivatives of 7β-hydroxycholesterol. The reaction of 7β-hydroxycholesterol with succinic anhydride has been carried out in order to render the derivatives water soluble, and the sodium or potassium salt has been formed from the resulting hemisuccinate.

Christ et al. (Anticancer Res. 1991, 11(1): 359-64) describe the preparation of phosphodiesters of 7β-hydroxycholesterol. These two salts exhibit an antitumor activity and are water soluble, however, are disadvantageous in that they do not remain stable in an aqueous solution.

The application EP 0 007 834 A1 relates to water soluble derivatives of cholesterol, particularly water soluble derivatives of 7β-hydroxycholesterol. This is achieved by compounds and complexes of albumin with organic dibasic half-esters of 7β-hydroxycholesterol.

The application EP 2 522 350 A1 relates to the use of an active substance combination consisting of a derivative of 1-diethylaminoethyl-3-chinoxalin-2-on and an oxysterol for the suppression of resistances in the treatment of cancer and for the enhancement of the immuno-potential in cancer, bacterial and viral diseases, autoimmune diseases, enhanced stress loading and environmental pollution.

Larsson et al., Free Radical Biology & Medicine 43 (2007), pp. 695-701 describes the conversion of 7β-hydroxycholesterol and 7-ketocholesterol in vivo, wherein both of which are surrogate markers for oxidative stress.

A disadvantage of the prior art is that the signal substance 7β-hydroxycholesterol that is produced in the body could not be used in an aqueous solution until now, but only two water soluble salts thereof (hydroxycholesteryl-bishemisuccinate-diethanolamine and 7β-hydroxycholesteryl-bishemisuccinate-disodium). Thus, Maier et al. (Anticancer Res. 1999, 19(5b), pp. 4251-4256) describe the induction of apoptosis by these two salts in human cell lines of colon carcinoma. These two salts are water soluble, however, are instable in an aqueous solution. After several hours, the substance starts to decompose and to flocculate. Furthermore, the way how the bishemisuccinate is acting in contrast to 7β-hydroxycholesterol and which are the additional side effects of ethanolamine upon administration to the human are not known.

Another disadvantage of the prior art is that 7β-hydroxycholesterol in oral form shall not be used because it is not known how much of the substance gets to the target site. Moreover, the absorption of 7β-hydroxycholesterol by the gastrointestinal tract is not known.

OBJECT OF THE INVENTION

Thus, there is a need for a targeted pharmaceutical application to solubilize or to maintain the substance 7β-hydroxycholesterol in an aqueous liquid and to subsequently intravenously administer it, e.g. per infusion.

DETAILED DESCRIPTION OF THE INVENTION

The present invention solves the technical problem by providing a composition comprising the pharmaceutically active substance 7β-hydroxycholesterol and a solvent system comprising a solvent and a solubilizing agent.

According to the present invention, the problem is solved by a pharmaceutical composition comprising:
a) 7β-hydroxycholesterol,
b) a water soluble organic solvent,
c) a non-ionic solubilizing agent.

In a preferred embodiment, the problem is solved by a pharmaceutical composition comprising:
a) 7β-hydroxycholesterol,
b) Propylene glycol and/or DMSO,
c) PEG hydrated castor oil.

7β-hydroxycholesterol ($C_{27}H_{46}O_2$) is a universally occurring signal substance having a molecular weight of 402.65294 g/mol that is produced in the thymus gland and that provides an anti-proliferative effect and that represents a universal signal substance of the endogenous immune defense. Thus, it is primarily used for cancer therapy of various tumors and for the general enhancement of the immune defense. It is a metabolic product that is formed by oxidation of cholesterol. In general, oxygenic derivatives of cholesterol (cholesterol) are referred to as oxysterols. The oxygenic functional groups (hydroxyl groups, ketone groups or epoxy groups) are attached to the carbon atoms of the cholesterol framework. 7β-hydroxycholesterol is characterized by the structural formula

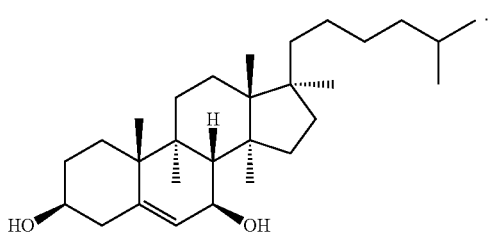

A suitable water soluble organic solvent is well known to the skilled person. According to the present invention, preferred water soluble organic solvents are polyethylene glycol 300, polyethylene glycol 400, (poly)propylene glycol, acetone, alcohols (e.g. ethanol, n-propanol, isopropanol), glycerol, N-methyl-2-pyrrolidone, dimethyl acetamide or dimethyl sulfoxide.

The use of propylene glycol (1,2-propanediol; $C_3H_8O_2$) as water soluble organic solvent is preferred. Propylene glycol is known as solvent and is used, according to the present invention, as solvent for 7β-hydroxycholesterol. It appears as a clear, colourless, substantially odourless and highly hygroscopic liquid having a molecular weight of 76.10 g/mol. Propylene glycol belongs to the class of polyvalent alkanols. It is water and ethanol miscible, however, immiscible with fatty oils. It is oxidation-sensitive at high temperatures above 150° C. Propylene glycol is a chiral compound (stereocentre at C2), which is mostly used as racemate. An advantage is that propylene glycol significantly improves the solubility of various substances and that it can provide a more stable dispersion of pharmaceuticals. Furthermore, it can often contribute to a significantly enhanced absorption of various active substances. The antimicrobial effect often obviates the use of additional preservative agents. Moreover propylene glycol is known to be included in injectable formulations of various pharmaceuticals, however, it is known that it can cause local incompatibilities in specific concentrations (see Kruss B. (Acta Pharm. Technol. 35(4) (1989) 187-196)). At the site of injection, there may be painful swellings and tissue incompatibilities, which sometimes regress only after weeks. The irritation potential on the skin is highly dependent on concentration, wherein a small addition, however, is commonly considered as being tolerable. Thus, its use should be made at a suitable concentration. According to the present invention, in the infusion solution to prepare, its concentration is below the critical point (10-15%) that causes the irritations and, thus, the patient tolerates it. Propylene glycol is characterized by the structural formula

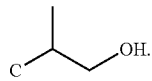

In a preferred embodiment, ethanol and/or acetone and/or dimethyl sulfoxide (DMSO; $C_2H_6OS$) can be alternatively or additionally used as solvents to propylene glycol. DMSO is an organic solvent and belongs to the class of sulfoxides. It is miscible with water and various organic solvents in any ratio. DMSO is characterized by a pharmaceutical effect (antiphlogistic and analgetic) and is often used in ointments, gels, tinctures and patches for the percutaneous treatment of blunt traumas and local conditions of pain.

7β-hydroxycholesterol exhibits an excellent solubility in a water soluble organic solvent (e.g. propylene glycol and/or DMSO and/or ethanol and/or acetone) and allows the solution to remain stable for years. However, if you want to dilute the solution of 7β-hydroxycholesterol/solvent in an aqueous liquid, e.g. for the provision of an infusion solution, the substance flocculates. Thus, the inventors use a solubilizing agent in order to maintain 7β-hydroxycholesterol in the later infusion solution in solution.

According to the present invention, the solubilizing agent is a non-ionic surface-active substance (surfactant). According to the present invention, preferred solubilizing agents are selected from PEG-hydrated castor oil (Cremophor®-series), D-tocopherol polyethylene glycol 1000-succinate (Kolliphor® TPGS), polysorbate 20 (Tween® 20), polysorbate 80 (Tween® 80), polyoxyethylated 12-hydroxystearic acid (Kolliphor® HS 15; Solutol® HS15), sorbitan monooleate (Span® 20), poloxamer 407 (Kolliphor® P 407), poloxamer 188 (Kolliphor® P 188), PEG 300 caprylic acid/capric glycerides (Softigen® 767), PEG 400 caprylic acid/capric glycerides (Labrasol®), PEG 300 oleic acid glycerides (Labrafil® M-1944CS), PEG 300 linoleic acid glycerides (Labrafil® M-2125CS), lauroyl polyoxyglycerides (Gellusire® 44/14), n-decanoic acid ester with 1,2,3-propane trioloctanoate (Softigen® 767), mono- or di-fatty acid esters of PEG 330, 400 or 1750.

According to the present invention, PEG hydrated castor oil has been found out as being a particularly suitable solubilizing agent. In particular, it has been shown that a stabilized liquid pharmaceutical formulation could be produced by using PEG-40 hydrated castor oil.

PEG hydrated castor oil is a derivative of polyethylene glycol (PEG) of hydrated castor oil and is an amber-coloured, slightly viscous liquid. Castor oil is a plant oil that is obtained from the seeds of the tropic miracle tree (*Ricinus communis*) of the family Euphorbiaceae. It consists of various trigylcerides and is also known as "polyoxyethylated castor oil" in pharmacy. During hydrogenation of the castor oil, hydrogen is added by using Raney nickel to the double bond of the ricinoleic acid. The hydroxyl group is maintained and a fat (castor wax), the triglyceride of 12-hydroxystearic acid, is obtained. Polyethylene glycols (PEG) are a synthetic raw material having ethylene oxide ($C_2H_4O$) as base component. Ethylene glycol, which is known as anti-freeze agent, derives from ethylene oxide with water. Ethylene glycol can further react with ethylene oxide and, thus, may form diethylene glycol and then polyethylene glycols (PEG) of various lengths having a correspondingly wide range of properties.

Commercial products of PEG hydrated castor oil are for example known on the basis of PEG7, PEG25, PEG35, PEG40, PEG50 and PEG60: Croduret™ 25 (Croda), Croduret™ 40 (Croda), Croduret™ 50 (Croda), Croduret™ 60 (Croda), Cremophor® RH 40 (BASF), Cremophor® RH 60 (BASF), Cremophor® RH 410 (BASF), Kolliphor EL or Cremophor EL (BASF), Emulgin® HRE 40 (BASF), Emulgin® HRE 455 (BASF) and EMAROL H40 (CISME, Italy). According to the present invention, PEG40 hydrated castor oil (Cremophor® RH40) is particularly suitable.

It has been found out that polyoxyethylated 12-hydroxystearic acid is another particularly suitable solubilizing agent. In particular, it could be shown that a stabilized liquid pharmaceutical formulation could be prepared by using polyoxyethylated 12-hydroxystearic acid.

Commercial products of polyoxyethylated 12-hydroxystearic acid are Kolliphor® HS15 (BASF) or Solutol® HS15. Kolliphor® HS15 consists of polyglycol monoesters and diesters of 12-hydroxystearic acid (=lipophilic portion) and about 30% free polyethylene glycol (=hydrophilic portion).

According to the present invention, the pharmaceutical composition comprises:
a) 0.1-2.0% (percent by weight; w/w) 7β-hydroxycholesterol, preferably 0.3-1.5% (w/w), more preferably 0.5-1.3% (w/w), particularly preferred 0.2, 0.3, 0.4, 0.5, 0.6, 0.7, 0.8, 0.9, 1.0, 1.1, 1.2, 1.3, 1.4, or 1.5% (w/w);
b) 68-97% (w/w) water soluble organic solvent (e.g. propylene glycol and/or DMSO and/or ethanol and/or acetone), preferably 70-95% (w/w), more preferably 75-90% (w/w), particularly preferred 70, 71, 72, 73, 74, 75, 76, 77, 78, 79, 80, 81, 82, 83, 84, 85, 86, 87, 88, 89, 90, 91, 92, 93, 94, or 95% (w/w);
c) 1-30% (w/w) solubilizing agent (e.g. PEG-hydrated castor oil or polyoxyethylated 12-hydroxystearic acid), preferably 5-25% (w/w), more preferably 5-20% (w/w), particularly preferred 5, 6, 7, 8, 9, 10, 11, 12, 13, 14, 15, 16, 17, 18, 19, or 20% (w/w).

Furthermore, the composition can comprise commonly used pharmaceutically acceptable additives, e.g. alcohols (preferably 1-15% (w/w) ethanol) or antioxidants (preferably 1-10% (w/w) caroverine hydrochloride, 1-10% (w/w) glutathione, 1-10% (w/w) vitamin C). Preferably, the composition can further comprise water insoluble lipids (e.g. castor oil, corn oil, cottonseed oil, olive oil, peanut oil, peppermint oil, safflower oil, sesame oil, soy bean oil, hydrogenated plant oils, medium-chain triglycerides from coconut oil and palm oil), organic liquids/semisolid substances (e.g. bees wax, D-tocopherol, oleic acid, medium-chain mono- or diglycerides), cyclodextrins (cyclodextrin, hydroxypropyl cyclodextrin, sulfobutylester cyclodextrin) and/or phospholipids (e.g. hydrogenated soy phosphatidylcholine, distearoylphosphatidylglycerol, L-dimyristoyl-phosphatidylcholine, L-dimyristoylphosphatidylglycerol).

These are preferred aqueous solutions in the preparation of intravenously administered preparations, i.e. infusion solutions, wherein it is possible to get them ready-for-use or to produce them just before use.

According to the present invention, the pharmaceutical composition can be mixed with an aqueous, commonly used liquid that is suitable for intravenous administration, preferably with physiological saline solution, a 5-10% glucose solution, Ringer's solution, Ringer's lactate solution, citrate buffer, purified water and/or HES to an infusion solution. The either ready-for-use solutions or the pharmaceutical composition (if the infusion solution is produced just before use) are sterilized and, subsequently, remain stable at room temperatures (<25° C.) for months. The sterilization is preferably performed by sterile filtration by means of filters and also by using an autoclave at a temperature of 120° C.

According to one embodiment of the inventive method, an appropriate amount of 7β-hydroxycholesterol is dissolved in a water soluble organic solvent (e.g. propylene glycol and/or DMSO and/or ethanol and/or acetone) by moderate heating at 30-40° C. for 15 min. The solubilizing agent, preferably PEG-40 hydrated castor oil or polyethoxylated 12-hydroxystearic acid, is subsequently added and the resulting concentrate is mixed well. This concentrate is added to the desired amount, preferably 100 ml, 200 ml and 400 ml, of the aqueous liquid, preferably glucose solution or physiologic saline solution. This solution is sterile filtrated and subsequently sterilized at above 100° C., preferably at 120° C.-140° C.

According to another embodiment of the inventive method, an appropriate amount of 7β-hydroxycholesterol is dissolved in a water soluble organic solvent (e.g. propylene glycol and/or DMSO and/or acetone and/or ethanol) by moderate heating at 30-40° C. for 15 min. The solubilizing agent, preferably PEG-40 hydrated castor oil or polyethoxylated 12-hydroxystearic acid, is subsequently added and the resulting concentrate is mixed well. This concentrate is sterile filtrated and subsequently sterilized at above 100° C., preferably at 120° C.-140° C. In a preferred embodiment, the concentrate can be diluted with an aqueous solution (e.g. water, citrate buffer, saline solution). The solution can be better sterilized because of the lower viscosity. The inventive composition is mixed in due time, e.g. just before the administration as an infusion, with an appropriate amount of the sterile aqueous liquid, e.g. sterile physiological saline solution or glucose solution, preferably 100 ml, 200 ml or 400 ml.

According to the present invention, the stability of 7β-hydroxycholesterol in propylene glycol and/or DMSO and/or ethanol and also PEG 40 hydrated castor oil or polyoxyethylated 12-hydroxystearic acid (Kolliphor® HS15) could be shown. The solution of β-hydroxycholesterol in propylene glycol and/or DMSO and/or ethanol and also PEG 40 hydrated castor oil or Kolliphor® HS15 could be easily mixed with physiologic saline solution and/or a glucose solution. It could be also shown that 7β-hydroxycholesterol remained stable for weeks and months in the infusion solution thus prepared.

The following compositions have been shown to be particularly preferred. In detail:
Propylene glycol
Optionally ethanol 96%
PEG40 hydrated castor oil
7β-hydroxycholesterol
Ethanol 96%
Kolliphor® HS15
Citrate buffer
7β-hydroxycholesterol
Both compositions can be preferably dissolved in physiological saline solution.

The addition of citrate buffer is often preferred because thereby a desired pH-value can be easily adjusted and maintained.

The inventive composition is particularly used as infusion for the therapy of tumors of all phenotypes, for the suppression of resistances in the treatment of cancer, for the enhancement of the general immuno-potential, for the treatment of bacterial and viral diseases, autoimmune diseases and also enhanced stress loading and environmental pollutions. The administration is performed by using standard procedures for intravenous administration, in particular as infusion.

It has been found out that it is particular preferred to administer the composition as an infusion within a time interval, e.g. 2-6 hours, preferably about 4 hours, to the administration of caroverine in capsule form (1-[2-(diethylamino)ethyl]-3-(4-methoxybenzyl)quinoxaline-2(1H)-one) or Synoverine®-capsules (7β-hydroxycholesterol+caroverine). It is preferred to administer the inventive infusion about 4 hours prior to the administration of the caroverine- or Synoverine®-capsules.

EXAMPLES

The present invention is described in detail in the following examples, which are not to be construed as being limiting.

Example 1

| | |
|---|---|
| Ethanol 96% | 0.3 g |
| Propylene glycol | 2.0 g |
| PEG40 hydrated castor oil | 0.5 g |
| 7β-hydroxycholesterol | 0.01 g |
| Physiological saline solution (or a 5% glucose solution) | ad 100 ml |

Example 2

| | |
|---|---|
| Propylene glycol | 20 g |
| PEG40 hydrated castor oil | 2 g |
| 7β-hydroxycholesterol | 0.06 g |
| Physiological saline solution (or a 5% glucose solution) | ad 200 ml |

Example 3

| | |
|---|---|
| Propylene glycol | 20 g |
| PEG40 hydrated castor oil | 2 g |
| 7β-hydroxycholesterol | 0.04 g |
| Physiological saline solution (or a 5% glucose solution) | ad 400 ml |

Example 4

| | |
|---|---|
| Propylene glycol | 7 g |
| PEG40 hydrated castor oil | 1.5 g |
| 7β-hydroxycholesterol | 0.04 g |
| Physiological saline solution (or a 5% glucose solution) | ad 200 ml |

Example 5

| | |
|---|---|
| Propylene glycol | 20 g |
| PEG40 hydrated castor oil | 1 g |
| 7β-hydroxycholesterol | 0.04 g |
| Physiological saline solution | ad 50 ml |

Example 6

| | |
|---|---|
| Dimethylsulfoxide (DMSO) | 20 g |
| PEG40 hydrated castor oil | 1 g |
| 7β-hydroxycholesterol | 0.04 g |
| Physiological saline solution | ad 50 ml |

Example 7

| | |
|---|---|
| Dimethylsulfoxide (DMSO) | 10 g |
| Propylene glycol | 10 g |
| PEG40 hydrated castor oil | 1 g |
| 7β-hydroxycholesterol | 0.04 g |
| Physiological saline solution | ad 50 ml |

Example 8

| | |
|---|---|
| Ethanol 96% | 0.3 g |
| Kolliphor ® HS 15 | 4.0 g |
| Citrate buffer | 4.0 g |
| 7β-hydroxycholesterol | 0.04 g |
| Physiological saline solution (or a 5% glucose solution) | ad 100 ml |

Example 9

| | |
|---|---|
| Ethanol 96% | 0.3 g |
| Kolliphor ® HS 15 | 4.0 g |
| Purified water | 4.0 g |
| 7β-hydroxycholesterol | 0.04 g |
| Physiological saline solution (or a 5% glucose solution) | ad 100 ml |

Example 10

| | |
|---|---|
| Propylene glycol | 1.0 g |
| Kolliphor ® HS 15 | 4.0 g |
| Purified water | 4.0 g |
| 7β-hydroxycholesterol | 0.04 g |
| Physiological saline solution (or a 5% glucose solution) | ad 100 ml |

Example 11

| | |
|---|---|
| DMSO | 1.0 g |
| Kolliphor ® HS 15 | 4.0 g |
| Purified water or citrate buffer | 4.0 g |
| 7β-hydroxycholesterol | 0.04 g |
| Physiological saline solution (or a 5% glucose solution) | ad 100 ml |

Example 12

Stability studies:

After sterilization at 120° C., neither the concentrate nor the readily prepared infusion solution (physiological saline solution) showed a decomposition of 7β-hydroxycholesterol. This means that 7β-hydroxycholesterol remained stable, even at this high thermal stress. A storing of the concentrate at 40° C. for 3 months did not show a decomposition of 7β-hydroxycholesterol either. The solution has been stored in glass vials.

A readily prepared infusion solution (on the basis of physiological saline solution) has been stored at room temperature (<25° C.) for 3 months. The solution remained clear, there was no flocculation. After storage, a decrease of the content of 7β-hydroxycholesterol could not be determined by using HPLC.

The invention claimed is:

1. A pharmaceutical composition comprising:
   (a) 0.1-2.0% (w/w) 7β-hydroxycholesterol,
   (b) 68-97% (w/w) of a water soluble organic solvent of propylene glycol and/or DMSO and/or ethanol and/or acetone, and
   (c) 1-30% (w/w) of a solubilizing agent of PEG hydrated castor oil or polyoxyethylated 12-hydroxystearic acid.

2. A pharmaceutical composition comprising:
   0.1-2.0% (w/w) 7β-hydroxycholesterol,
   68-97% (w/w) propylene glycol and/or DMSO,
   1-30% (w/w) PEG hydrated castor oil.

3. The pharmaceutical composition according to claim 1, wherein the composition further comprises one or more alcohols and/or antioxidants.

4. The pharmaceutical composition according to claim 1, wherein the PEG hydrated castor oil is PEG40 hydrated castor oil.

5. A method for preparing the pharmaceutical composition according to claim 1, comprising dissolving 7β-hydroxycholesterol by moderate heating in the water soluble organic solvent, and by adding the solubilizing agent.

6. The method according to claim 5, wherein the pharmaceutical composition is sterile filtered and is sterilized at 120° C.-140° C.

7. An infusion solution comprising the pharmaceutical composition according to claim 1 and an aqueous liquid.

8. The infusion solution of claim 7, wherein the aqueous liquid is physiological saline solution, glucose solution or Ringer's solution.

* * * * *